US009849271B2

(12) United States Patent
Kato et al.

(10) Patent No.: US 9,849,271 B2
(45) Date of Patent: Dec. 26, 2017

(54) NEEDLE-LIKE MATERIAL AND METHOD FOR MANUFACTURING NEEDLE-LIKE MATERIAL

(71) Applicant: TOPPAN PRINTING CO., LTD., Taito-ku (JP)

(72) Inventors: Hiroyuki Kato, Taito-ku (JP); Takako Yamamoto, Taito-ku (JP); Yoshikazu Taroura, Taito-ku (JP)

(73) Assignee: TOPPAN PRINTING CO., LTD., Taito-ku (JP)

( * ) Notice: Subject to any disclaimer, the term of this patent is extended or adjusted under 35 U.S.C. 154(b) by 582 days.

(21) Appl. No.: 14/470,078

(22) Filed: Aug. 27, 2014

(65) Prior Publication Data

US 2014/0361459 A1    Dec. 11, 2014

Related U.S. Application Data

(63) Continuation of application No. PCT/JP2013/052409, filed on Feb. 1, 2013.

(30) Foreign Application Priority Data

Feb. 29, 2012 (JP) ................. 2012-044485
Mar. 9, 2012 (JP) ................. 2012-053700
Jun. 22, 2012 (JP) ................. 2012-140754

(51) Int. Cl.
*A61M 37/00* (2006.01)
*B29C 41/12* (2006.01)
(Continued)

(52) U.S. Cl.
CPC ....... *A61M 37/0015* (2013.01); *A61K 9/0021* (2013.01); *A61K 47/12* (2013.01);
(Continued)

(58) Field of Classification Search
CPC . B29C 45/1808; B29C 47/705; B29C 47/369; B29C 47/362; B29C 47/54;
(Continued)

(56) References Cited

U.S. PATENT DOCUMENTS 8,062,568 B2 * 11/2011 Lee ..................... B81C 99/0025
264/219
8,383,027 B2 * 2/2013 Ogawa ................. B29C 33/306
156/60

(Continued)

FOREIGN PATENT DOCUMENTS

CN   101687090 A   3/2010
JP   48-093192 A   12/1973
(Continued)

OTHER PUBLICATIONS

Extended European Search Report dated Oct. 6, 2015 in Patent Application No. 13755630.4.
(Continued)

*Primary Examiner* — Nahida Sultana
(74) *Attorney, Agent, or Firm* — Oblon, McClelland, Maier & Neustadt, L.L.P.

(57) ABSTRACT

A needle-shaped structure includes a needle-shaped projection and a support substrate supporting the projection wherein the projection contains at least a chitosan and an organic acid, places a low burden on a living body and is able to keep the microscopic form after puncture into the skin.

20 Claims, 7 Drawing Sheets

(51) Int. Cl.
 B29C 39/00 (2006.01)
 A61K 9/00 (2006.01)
 A61K 47/12 (2006.01)
 A61K 47/36 (2006.01)

(52) U.S. Cl.
 CPC ............ *A61K 47/36* (2013.01); *B29C 39/003* (2013.01); *B29C 41/12* (2013.01); *A61M 2037/0046* (2013.01); *A61M 2037/0053* (2013.01); *B29K 2005/00* (2013.01); *F04C 2270/041* (2013.01)

(58) Field of Classification Search
 CPC . B29C 47/702; B29C 47/366; B29C 45/0013; B29C 47/0016; B29C 47/0021; B01F 3/1221; B01F 5/0644; B01F 7/086; B01F 15/0404; B01F 5/0601
 USPC ........ 264/219, 220, 225, 226, 227; 425/588, 425/219, 385
 See application file for complete search history.

(56) References Cited

U.S. PATENT DOCUMENTS

| | | | | |
|---|---|---|---|---|
| 8,944,804 | B2* | 2/2015 | Robeson | H01L 29/06 264/2.5 |
| 2002/0127385 | A1* | 9/2002 | Topolkaraev | A61F 13/15211 428/315.5 |
| 2002/0138049 | A1* | 9/2002 | Allen | A61B 5/14514 604/272 |
| 2007/0191761 | A1* | 8/2007 | Boone | A61B 17/205 604/46 |
| 2008/0269685 | A1 | 10/2008 | Singh et al. | |
| 2009/0042834 | A1* | 2/2009 | Karageozian | A61K 31/728 514/56 |
| 2009/0234301 | A1* | 9/2009 | Tomono | A61M 37/0015 604/272 |
| 2010/0072661 | A1* | 3/2010 | Cho | B29C 33/3842 264/219 |
| 2010/0155988 | A1* | 6/2010 | Keil | B29C 33/3857 264/219 |
| 2012/0027837 | A1 | 2/2012 | DeMuth et al. | |
| 2013/0292868 | A1 | 11/2013 | Singh et al. | |
| 2016/0129164 | A1* | 5/2016 | Lee | A61K 9/0021 604/173 |
| 2017/0080196 | A1* | 3/2017 | Lee | A61C 19/063 |

FOREIGN PATENT DOCUMENTS

| | | |
|---|---|---|
| JP | 2006-500973 A | 1/2006 |
| JP | 2009-254814 A | 11/2009 |
| JP | 2010-213845 A | 9/2010 |
| JP | 2010-535589 A | 11/2010 |
| KR | 10-2011-0022554 A | 3/2011 |
| WO | WO 2006/080508 A1 | 8/2006 |
| WO | WO 2008/004597 | 1/2008 |
| WO | WO 2008/013282 | 1/2008 |
| WO | WO 2008/130587 A2 | 10/2008 |

OTHER PUBLICATIONS

Combined Office Action and Search Report dated Oct. 23, 2015 in Chinese Patent Application No. 201380011237.3 (with English language translation and English Translation of Category of Cited Documents).

International Search Report dated May 14, 2013 in PCT/JP2013/052409 (with English Translation).

Office Action dated May 30, 2017 in Japanese Patent Application No. 2014-502087 (with English language translation).

* cited by examiner

NEEDLE-LIKE MATERIAL AND METHOD FOR MANUFACTURING NEEDLE-LIKE MATERIAL

CROSS-REFERENCE TO RELATED APPLICATIONS

The present application is a continuation of International Application No. PCT/JP2013/52409, filed Feb. 1, 2013, which is based upon and claims the benefits of priority to Japanese Application No. 2012-044485, filed Feb. 29, 2012, Japanese Application No. 2012-053700, filed Mar. 9, 2012, and Japanese Application No. 2012-140754, filed Jun. 22, 2012. The entire contents of all of the above applications are incorporated herein by reference.

TECHNICAL FIELD

This invention relates to a needle-shaped structure and a method for fabricating same.

BACKGROUND ART

A percutaneous absorption method where a delivery of a drug, etc. is infiltrated from the skin for administration thereof to the body is a method capable of simply administering the delivery without giving a pain to the human body.

Japanese Laid-open Patent Application S48-93192 describes a method related to the field of percutaneous administration where a needle-shaped structure formed thereon with needles on the order of μm is used for puncture into the skin so as to administer a drug or the like inside the skin.

International Publication Pamphlet No. 2008/013282 describes a method of making a needle-shaped structure. In this method, the needle-shaped structure is fabricated by making an original plate according to a machine processing, forming a transfer plate from the original plate and subjecting to transfer molding by use of the transfer plate.

International Publication Pamphlet No. 2008/004597 describes another method of making a needle-shaped structure. In this method, the needle-shaped structure is made by making an original plate by an etching method, forming a transfer plate from the original plate and subjecting to transfer molding by use of the transfer plate.

SUMMARY OF INVENTION

According to one aspect of the present invention, a method of producing a needle-shaped structure having a support substrate and a needle-shaped projection projected from the support substrate, includes preparing a liquid material including a chitosan component and an acid, applying the liquid material onto an intaglio plate having a needle-shaped recess, solidifying the liquid material applied onto the intaglio plate such that a solidified article made from the liquid material is obtained, separating the solidified article from the intaglio plate, and immersing separated solidified article in an aqueous alcohol solution.

According to another aspect of the present invention, a method of producing a needle-shaped structure having a support substrate and a needle-shaped projection projected from the support substrate, includes preparing a liquid material including a chitosan component and an acid, applying a liquid material onto an intaglio plate having a needle-shaped recess, solidifying the liquid material applied onto the intaglio plate such that a solidified article made from the liquid material is obtained, separating the solidified article from the intaglio plate, and acetylating the chitosan component in separated solidified article.

According to another aspect of the present invention, a method of producing a needle-shaped structure having a support substrate and a needle-shaped projection projected from the support substrate, includes preparing a liquid material including a chitosan component, a first acid, and a second acid, applying the liquid material onto an intaglio plate having a needle-shaped recess, solidifying the liquid material such that a solidified article made from the liquid material is obtained, separating the solidified article from the intaglio plate, and immersing separated solidified article in an aqueous alcohol solution. The first acid is a tri- or higher valent carboxylic acid or a dicarboxylic acid having a number average molecular weight of at not less than 110, and the second acid is a monocarboxylic acid or a dicarboxylic acid, having a number average molecular weight of at less than 110.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
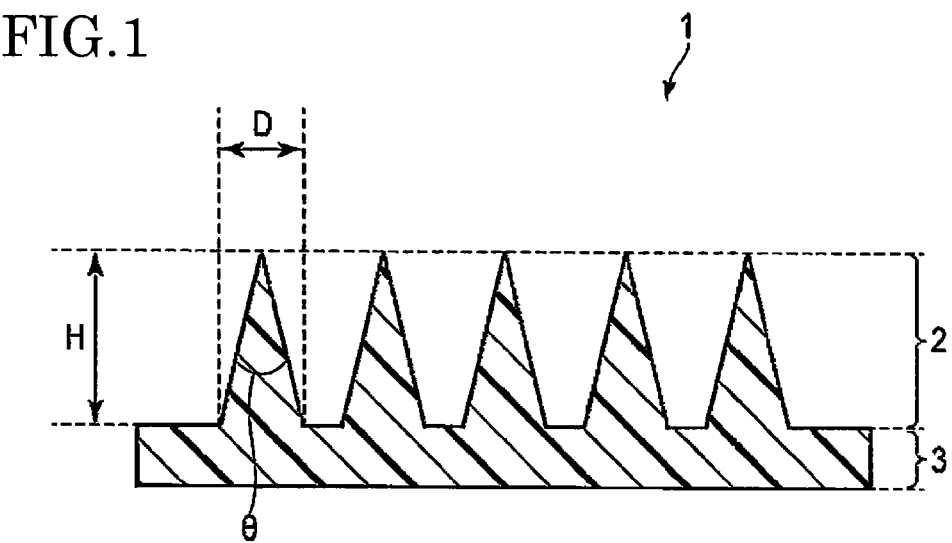
FIG. 1 is a schematic sectional view of a needle-shaped structure related to a first embodiment.

The embodiments will now be described with reference to the accompanying drawings, wherein like reference numerals designate corresponding or identical elements throughout the various drawings.

The needle-shaped structure and the method for making the needle-shaped structure according to the embodiments of the invention are now described in detail.

First Embodiment

The needle-shaped structure related to the first embodiment includes a needle-shaped projection and a support substrate supporting the projection, the projection, at least, containing a chitosan and citric acid.

The needle-shaped structure according to the first embodiment is more particularly described with reference to FIG. 1. A needle-shaped structure 1 is provided with needle-shaped projections 2 and a support substrate supporting the projections 2. The projections 2 contain at least a chitosan and citric acid.

The chitosan that is a main component contained in the material for the projection possesses bioadaptability, for which there can be used at least one or more selected from the group consisting of chitosan, chitin/chitosan, chitin/a chitosan derivative, glucosamine and a glucosamine derivative. Although there is no clear boundary line between chitin and chitosan, it is usual that those of chitin whose degree of deacetylation is not less than 70 are called chitosan. The deacetylation can be carried out by known techniques.

Usable chitosan, chitin/chitosan, chitin/chitosan derivatives and glucosamine derivatives are those which are derived from crustacean such as crabs, shrimps and the like and also derived from fungus- and microorganism-producing plants and which are obtained therefrom used as a starting material. Chitosan, chitin/chitosan and chitin/chitosan derivatives show a beauty effect on the skin and has antiseptic and bactericidal effects, and can thus be preferably used as a material for the needle-shaped projection.

The projection material contains citric acid aside from a chitosan. Citric acid is an acid that is safe to living bodies and has been widely known as a food additive. Accordingly, there is obtained such an effect as to provide a sense of safety on the part of a user.

The needle-shaped structure containing a chitosan and citric aid according to the first embodiment is broadly classified into type (1) which is sparingly soluble in water after having subjected to an immersion step in an aqueous alcohol solution described hereinafter and type (2) which is soluble in water without subjecting to the alcohol immersion step.

The needle-shaped structure of the type (1) which is sparingly soluble in water is such that when punctured into the skin, the needle-shaped structure is not dissolved. Thus, when the needle-shaped structure is punctured into the skin and removed from the skin, a delivery can be administered to the skin. Alternatively, if a delivery is beforehand coated onto and formed on the surface of the needle-shaped structure and this needle-shaped structure, formed with the delivery on the surface thereof, is punctured into the skin, the delivery may also be administered to the skin.

On the other hand, the needle-shaped structure of the type (2), which is soluble in water, is dissolved upon puncturing into the skin. With the soluble needle-shaped structure, the needle-shaped structure containing a chitosan and citric acid may further contain a delivery. Moreover, since the needle-shaped structure further containing a delivery is dissolved upon puncturing into the skin, the delivery can be administered into the skin. When the needle-shaped structure soluble in water is once punctured, the projection disappears, so that there can be obtained such an effect that a user of the needle-shaped structure can be prevented from being punctured twice.

It will be noted that for the delivery used in practicing the embodiments of the invention, mention is made, for example, of physiologically active substances, cosmetic compositions and the like. The delivery may contain biologics. The biologics used herein means a classification of drugs making use of raw materials or material derived from the cells, cell tissues and the like of humans and animals.

The first embodiment has such an effect that there can be obtained a warpage-free needle-shaped structure. If the needle-shaped structure undergoes warpage, the performance of puncture into the skin lowers and thus, the structure is preferably free of warpage.

Where the needle-shaped structure is formed of a chitosan and citric acid, the color shade of the needle-shaped structure changes depending on the amount of citric acid. This can bring about such an effect that the process control and quality control can be made according to the color shade. Especially, in case where the amount of citric acid is determined within a specified range as will be described hereinafter, the needle-shaped structure can be rendered white for optimum use in cosmetic or medical products.

The amount of citric acid in the projection is preferably within a range of not less than 0.5 wt % to 40 wt %. When the amount of citric acid in the needle-shaped structure is set at not larger than 40 wt %, the resulting needle-shaped structure is prevented from being formed as a soluble needle-shaped structure that is dissolved in a living body and thus, such a microscopic configuration of the needle-shaped structure can be held after puncture.

The amount of citric acid in the projection is more preferably within a range of not less than 0.5 wt % to not larger than 30 wt %. When the amount of citric acid is set at not larger than 30 wt %, the needle-shaped structure can be kept as white. Eventually, cleanliness is obtained, so that a sense of resistance can be mitigated upon puncture into the skin of a user.

It will be noted that a less amount of the citric acid contained in the needle-shaped structure is more preferred from the standpoint of preventing the needle-shaped structure from being dissolved in a living body. In this regard, however, if the amount of citric acid is less than 0.5 wt %, there is concern that productivity lowers for removal of citric acid.

The needle-shaped structure according to the first embodiment may further contain other type of organic acid aside from a chitosan and citric acid. Examples of other type of organic acid to be contained in the needle-shaped structure include acetic acid, succinic acid, lactic acid, glyoxylic acid, tartaric acid, pyruvic acid, oxalosuccinic acid, oxaloacetic acid, acetoacetic acid, levulinic acid, and oxoglutaric acid. The content (wt %) of the organic acid in the needle-shaped structure can be determined according to ion chromatography.

In the needle-shaped structure of the first embodiment, a projection 1 may have a shape suited for puncture into the skin. The projection 1 has a shape such as, for example, of a cone, a pyramid, a cylinder, a prism, a pencil form (wherein the body is cylindrical with its tip being conical or pyramidal) or the like. The projection may be either (1) in a form of standing singly on a support substrate or (2) in a form of standing plurally on a support substrate.

Where plural projections stand on a support substrate, individual projections should preferably be arranged in arrays. The "array" used herein means a state where the respective unit needle-shaped structures are set in array. For instance, mention is made of lattice arrangement, closest packing arrangement, concentric arrangement, random arrangement and the like.

For the use of the needle-shaped structure of the first embodiment, an applicator for fixing an insertion position and direction of the needle-shaped structure may be attached.

The needle-shaped structure of the first embodiment may be provided with a hole at the projection thereof. The hole may be either a through-hole passing through to the back side of the support substrate or a non-through hole. Additionally, the support substrate per se may be provided with a hole or holes. The hole may be either a through-hole passing through to the back side of the support substrate or a non-through hole.

As to the dimension of the needle-shaped structure of the first embodiment, the projection preferably has a fineness and length suited for forming a puncture hole in the skin.

More particularly, a height H of the projection 2 shown in FIG. 1 should preferably be within a range of from not less than 10 μm to not larger than 1000 μm. The height H of the projection means a distance between the support substrate and the tip end portion of the projection.

The height H of the projection is preferably determined while taking it into account how deep the puncture hole formed at the time when the needle-shaped structure is punctured within the above range goes into the skin.

Especially, where the puncture hole formed when the needle-shaped structure is punctured is kept "in the stratum corneum", the height of the projection of the needle-shaped structure is preferably within a range of not less than 10 μm to not larger than 300 μm, more preferably within a range of not less than 30 μm to not larger than 200 μm.

Where the puncture hole formed when the needle-shaped structure is used for puncture is kept to "a length sufficient to pass through the stratum corneum but not to arrive at the nervous layer", the height H of the projection of the needle-shaped structure is preferably within a range of not less than 200 μm to not larger than 700 μm, more preferably from not less than 200 μm to not larger than 500 μm, and much more preferably from not less than 200 μm to not larger than 300 μm.

Further, where the puncture hole formed when the needle-shaped structure is punctured is set at "a length thereof sufficient to arrive at the dermis", the height H of the projection of the needle-shaped structure is preferably within a range of not less than 200 μm to not larger than 500 μm. Moreover, where the puncture hole formed when the needle-shaped structure is punctured is set at "a length thereof sufficient to arrive at the epidermis", the height H of the projection of the needle-shaped structure is preferably within a range of not less than 200 μm to not larger than 300 μm.

A width D of the projection is preferably within a range of not less than 0.1 μm to not larger than 300 μm. The width D of the projection should preferably be determined while taking it into account how deep the puncture hole, which is formed at the time when the needle-shaped structure is punctured within the above range, goes into the skin.

The width D of the projection means a maximum length among lengths of the projection in contact with the support substrate when the projection is projected parallel to the substrate surface. For instance, where the projection is conical in shape, the diameter of a circle formed at the contact surface between the projection and the support substrate becomes width D. Where the projection is quadrilateral in shape, the diagonal of a square formed at the contact surface between the projection and the support substrate becomes width D. Additionally, where the projection is cylindrical, the diameter of a circle formed at the contact surface between the projection and the support substrate becomes width D. Where the projection is shaped as a square prism, the diagonal of a square formed at the contact surface between the projection and the support substrate becomes width D.

The aspect ratio is preferably within a range of not less than 1 to not larger than 10. Using the length H and width D of the projection, the aspect ration is defined such that $A=H/D$.

In the needle-shaped structure according to the embodiment, the projection is configured to have a tip angle like a cone. When the stratum corneum is passed through, the tip angle θ of the projection is preferably within a range of from not less than 5° to not larger than 30°, more preferably from not less than 10° to not larger than 20°. It will be noted that the tip angle θ indicates a maximum angle chosen from angles (apex angles) created when the projection is projected parallel to the surface of the support substrate.

In the needle-shaped structure of the first embodiment, it is preferred that the support substrate is made of the same material as the projection. When the support substrate and the projection are made of the same material, respectively, it becomes possible to form the support substrate and the projection integrally.

The support substrate may have a multilayered structure wherein a material different in type from the material for the projection may be laminated as a lower layer. If plural types of materials are laminated, there can be provided a support substrate making use of physical properties of plural types of materials as described below.

(1) With a support substrate wherein an upper layer on which the projection is formed is formed of the same material as the projection and a lower layer is formed of a flexible material, the substrate can be folded in a roll fashion.

(2) A support substrate wherein an upper layer is formed of a material whose ductility is greater than that of a lower layer can be folded in a roll fashion.

(3) A support substrate wherein a lower layer is formed of a material whose shrinkage is smaller than an upper layer can also be folded in a roll fashion.

(4) If needle-shaped structures each having a support substrate whose undermost layer is formed of a flexible material are stored as superposed, projections can be prevented from breakage.

Net, a method for fabricating a needle-shaped structure according to the first embodiment is described in detail.

<Step of Preparing an Intaglio Plate>

An original plate which determines the shape of a needle-shaped structure is made, and an intaglio plate whose pattern is inverted relative to the shape of a desired needle-shaped structure is made out of the original plate. The original plate, with which the shape of needle-shaped structure is determined, can be made according to known techniques although depending on the shape of needle-shaped structure. The original plate may be formed by use of microfabrication techniques. Examples of the microfabrication technique include a lithographic technique, a wet etching technique, a dry etching technique, a sand blasting technique, a laser processing technique, a precision machining technique and the like. For the formation of an intaglio plate from the original plate, known shape transfer methods can be used. For instance, mention is made of (1) formation of an Ni intaglio plate by an Ni electroforming process, (2) transfer formation using a molten resin, and the like.

<Step of Preparing a Liquid Material for Needle-Shaped Structure>

Biodegradable chitosan is dissolved in an aqueous citric acid solution to prepare a liquid needle-shaped structure material containing a chitosan and citric acid.

The liquid needle-shaped structure material should preferably have fluidity sufficient to apply it onto the intaglio plate, or may be in a gel form.

The formulation ratio between chitosan and citric acid is such that an amount of citric acid is appropriately controlled so that there is obtained a liquid needle-shaped structure material wherein a chitosan is well dissolved. More particularly, the formulation ratio between the chitosan and citric acid is preferably at 30-50 wt % of chitosan and 50-70 wt % of citric acid.

<Step of Filling the Liquid Needle-Shaped Structure Material>

The liquid needle-shaped material is filled onto the intaglio plate. The application method can be appropriately selected from known procedures depending on the shape and size of the intaglio plate. For instance, there can be used a spin coating method, a method using a dispenser, a casting method and the like. For the filling, an ambient environment around the intaglio plate may be kept either under reduced pressure or under vacuum.

<Step of Solidifying the Liquid Needle-Shaped Structure Material>

The liquid needle-shaped structure material filled onto the intaglio plate is dried for solidification to obtain a solidified article made of the needle-shaped material. Although the solidification may be completed under drying at a normal temperature, it is preferred to use heat drying so as to shorten the production time. In order to avoid the bubbles being left in the needle-shaped structure, the heating temperature is preferably set at a level not permitting the aqueous solution to be boiled. In this sense, the heating temperature is preferably with a range of from 50° C. to 90° C. Heating may be carried out by any of known heating means. For instance, there can be used a hot plate mounting the intaglio plate filled with a liquid needle-shaped structure material thereon.

<Step of Removing the Solidified Article Made of the Needle-Shaped Structure Material>

The solidified article made of the needle-shaped structure material is removed from the intaglio plate. The thus removed solidified article has a final shape of needle-shaped structure.

For the removal, there can be used, for example, a method wherein the solidified material is peeled off from the intaglio plate by physical force, a method wherein the intaglio plate is chemically, selectively dissolved out, and the like.

In the needle-shaped structure of the first embodiment, in order to prevent the structure from being dissolved inside a living body and keep a microscopic shape of the needle-shaped structure after puncture, it is preferred that the removed solidified article made of the needle-shaped structure is immersed in an aqueous alcohol solution to partially remove the organic acid in the structure.

<Immersion of the Solidified Article Made of the Needle-Shaped Structure Material in an Aqueous Alcohol Solution>

The removed solidified article made of the needle-shaped structure material is immersed in an aqueous alcohol solution.

The alcohol may be one which is miscible with water, for which there can be used, for example, ethanol, methanol and propanol. Of these, ethanol is preferred from the standpoint of biosafety.

The aqueous alcohol solution preferably has an alcohol concentration of 50-90 wt %. If the alcohol concentration in the aqueous alcohol solution exceeds 90 wt %, a difficulty is involved in that the acid contained in the solidified article made of the needle-shaped structure material is well dissolved out, with concern that the immersion time is prolonged thereby lowering productivity. On the other hand, if the alcohol concentration in the aqueous alcohol solution is less than 50 wt %, there is concern that the resulting needle-shaped structure is swollen.

Although the aqueous alcohol solution may be used at room temperature, heating is preferred so as to promote the dissolution of the acid in the solidified article. Where an aqueous ethanol solution is used as an aqueous alcohol solution, it is preferred to heat it within a range of from 40° C. to 60° C.

Although the time for immersing the solidified article in the aqueous alcohol solution depends on the type of alcohol, its concentration and the like and cannot be necessarily defined, it is preferred to set the time at 8 hours-5 days.

When the solidified article is immersed in an aqueous alcohol solution, a multiple-step treatment is preferred using successive immersions in an aqueous alcohol solution of a high concentration and then in an aqueous alcohol solution of a lower concentration. For instance, a solidified article is immersed in an aqueous alcohol solution whose concentration is at not less than 70 wt % to not larger than 90 wt %, followed by transferring the solidified article for immersion in an aqueous alcohol solution with a concentration of not less than 50 wt % to not larger than 70 wt %. Such a multiple-step immersion treatment of the solidified article first with a highly concentrated aqueous alcohol solution and then with an aqueous alcohol solution of a lower concentration suppresses the dissolution of chitosan serving as a main component of the solidified article thereby ensuring shape stabilization. At the same time, it is enabled to promote the dissolution of the acid from the solidified article.

In order to make a needle-shaped structure of a chitosan by use of an intaglio plate, the chitosan needs to be dissolved in an aqueous solution of an acid to prepare a liquid needle-shaped structure material beforehand. Such a liquid needle-shaped structure material contains not only a chitosan, but also an acid. Accordingly, the solidified article having the shape of the needle-shaped structure, which is obtained by drying, solidifying and removing from an intaglio plate after forming with an intaglio plate, contains not only a chitosan, but also the acid.

The needle-shaped structure, which has not been subjected to alcohol immersion, contains an acid and is thus poor in water resistance. If this structure is used as it is, dissolution occurs by contact with moisture or immersion in water. Eventually, dissolution occurs in vivo.

On the other hand, a bioadaptable chitosan, which has been subjected to alcohol immersion, has sparing solubility in water. Accordingly, there can be fabricated a needle-shaped structure which is sparingly soluble in water, shows a high water resistance, can be punctured without damaging the skin, and is able to keep a microscopic shape (with a fine three-dimensional structure on the order of μm) after puncture and thus has a low body burden.

It will be noted that in the first embodiment, the term "sparing solubility of the needle-shaped structure in water" means that "after the needle-shaped structure has been immersed in a phosphate buffer solution (PBS) with a pH of 7.5 for 24 hours, a reduced volume of the projection of the needle-shaped structure is at not larger than 5% of the volume prior to the immersion". On the other hand, the case where the above conditions are not satisfied means that "the needle-shaped structure is soluble in water".

Second Embodiment

Next, a method for fabricating a needle-shaped structure according to a second embodiment is described in detail.

The needle-shaped structure has a needle-shaped projection and a support substrate supporting the projection as has been illustrated with respect to the first embodiment. At least the projection is formed of a material containing a chitosan.

The details of the projection described herein are the same as those set out in the first embodiment.

The present inventors have found that for the preparation of a needle-shaped structure from a liquid needle-shaped structure material containing a chitosan and an acid, when water-resistance treatment is carried out after the formation of the needle-shaped structure, there can be made a needle-shaped structure that shows a high water resistance, can be punctured into the skin without breakage, and is able to keep a microscopic shape (a fine three-dimensional structure on the order of μm) after puncture, thus resulting in a low body burden.

More particularly, the water-resistance treatment is performed by a procedure wherein a solidified article of a needle-shaped structure is formed from a liquid needle-shaped structure material containing a chitosan and an acid and this solidified article is immersed in an aqueous alcohol solution, or by a procedure wherein a solidified article of a needle-shaped structure is formed from a liquid needle-shaped structure material containing a chitosan and an acid and the solidified article is subjected to an acetylation step. It has been found that according to this water-resistance treatment, there can be fabricated a needle-shaped structure that is sparingly soluble in water and shows a high water resistance, can be punctured into the skin without breakage, and is able to keep a microscopic shape after the puncture, thus resulting in a low body burden.

At least a projection of the needle-shaped structure fabricated according to the second embodiment is sparingly soluble in water. The term "at least a projection of the needle-shaped structure is sparingly soluble in a water solvent" used herein means that "after the needle-shaped structure is immersed in a phosphate buffer solution (PBS), a reduced volume of at least a projection of the needle-shaped structure is at not larger than 5% of the volume prior to the immersion".

The method for fabricating the needle-shaped structure according to the second embodiment is now described in detail according to the respective steps.

<Step of Making an Intaglio Plate>

An original plate which determines the form of a needle-shaped structure is made, and an intaglio plate whose pattern is inverted relative to the shape of a desired needle-shaped structure is made out of the original plate. This step is similar to as illustrated in the first embodiment.

<Step of Preparing a Liquid Material for Needle-Shaped Structure>

A bioadaptable chitosan is dissolved in an aqueous solution of an acid to preparing a liquid needle-shaped structure material containing a chitosan and the acid.

The liquid needle-shaped structure material preferably has a degree of fluidity sufficient to allow it to be passed onto the intaglio plate, or may be in a gel form.

The chitosan used may be a similar one as described in the first embodiment.

The acid may be either an organic acid or an inorganic acid. Examples of the organic acid include acetic acid, succinic acid, citric acid, lactic acid, tartaric acid, glyoxylic acid, pyruvic acid, oxalosuccinic acid, oxaloacetic acid, acetoacetic acid, levulinic acid and oxoglutaric acid. Examples of the inorganic acid include hydrochloric acid and sulfuric acid.

The formulation ratio between the chitosan and the acid can be appropriately controlled depending on the type of acid from the standpoint of obtaining a liquid needle-shaped structure material well dissolving chitosan therein.

<Step of Filling the Liquid Needle-Shaped Structure Material>

The liquid needle-shaped structure material is filled onto the intaglio plate. This filling procedure is similar to as described in the first embodiment.

<Step of Solidifying the Liquid Needle-Shaped Structure Material>

The liquid needle-shaped structure material filled onto the intaglio plate is dried and solidified to obtain a solidified article made of the needle-shaped structure material. This step is similar to as described in the first step.

<Step of Removing the Solidified Article Made of the Needle-Shaped Structure Material>

The solidified article made of the needle-shaped structure material is removed from the intaglio plate. The thus removed solidified article has a needle-shaped form that is a final one.

The removing method may include, for example, a method of removing the solidified articles from the intaglio plate by physical force, a method of chemically, selectively dissolving the intaglio plate, and the like.

<Step of Water Resistance Treatment of the Solidified Article Made of the Needle-Shaped Structure Material>

The solidified article made of the needle-shaped structure material is subjected to water-resistance treatment. The water-resistance treatment can be carried out by (1) a procedure of forming a solidified article of needle-shaped structure from a liquid needle-shape structure material containing a chitosan and an acid and immersing the solidified article in an aqueous alcohol solution, or (2) a procedure of forming a solidified article of needle-shaped structure from a liquid needle-shape structure material containing a chitosan and an acid and acetylating the solidified article.

<Water-Resistance Treatment (1)>

The solidified article of needle-shaped structure formed from the liquid needle-shaped structure material containing a chitosan and the acid is immersed in an aqueous alcohol solution.

The kind of alcohol and the concentration and temperature of the aqueous alcohol solution, in which the solidified article of needle-shaped structure is to be immersed, and the time of immersion of the solidified article in the aqueous alcohol solution are similar to as described in the first embodiment.

When the solidified article is immersed in an aqueous alcohol solution, it is preferred to use a plural-stage treatment wherein the article is successively immersed in an aqueous alcohol solution of high concentration and then in an aqueous alcohol solution of a lower concentration in the same way as illustrated in the first embodiment.

The bioadaptable chitosan has such a property as to be sparingly soluble in water. Thus, for the fabrication of a needle-shape structure of a chitosan by use of an intaglio plate, a liquid needle-shaped structure material is prepared by dissolving a chitosan in an aqueous solution of an acid beforehand. Such a liquid needle-shaped structure material contains not only a chitosan, but also the acid, so that the solidified article having a needle-shaped form obtained by drying and solidifying after forming with the intaglio plate and removing from the intaglio plate also contains not only a chitosan, but also the acid. The resulting solidified article is poor in water resistance because the acid is contained. If this is used as a needle-shaped structure as it is, it is dissolved by contact with moisture or immersion in water. As a consequence, not only a high body load arises through dissolution inside the body, but also a microscopic form of the needle-shaped structure cannot be kept after puncture.

According to the second embodiment, when the water-resistance treatment (1) is carried out against the solidified article, there can be made a needle-shaped structure which is sparingly soluble in water, shows high water resistance, can be punctured into the skin without breakage, is able to keep a microscopic form after puncture and places a low burden on a living body.

<Water-Resistance Treatment (2)>

The solidified article of the needle-shaped structure formed out of a liquid needle-shaped structure material containing a chitosan and an acid is acetylated.

For the acetylation of the removed solidified article made of the needle-shaped structure material, known procedures can be used. More particularly, the solidified article made of the needle-shaped material is immersed in a mixed solution of acetic anhydride and methanol and removed from the mixed solution, followed by immersion in methanol and dehydration to complete the acetylation.

The mixed solution is preferably prepared, for example, by mixing 10-20 wt % of acetic anhydride and 80-90 wt % of methanol.

According to the second embodiment adopting the water-resistance treatment (2), there can be fabricated a needle-shaped structure which is sparingly soluble in water, shows high water resistance, can be punctured into the skin without breakage, is able to keep a microscopic form after puncture and places a low burden on a living body.

More particularly, when the solidified article, which is obtained from a liquid needle-shaped structure material dissolving a bioadaptable chitosan in an aqueous solution of an acid and has a needle-shaped form, is acetylated, the amino group serving as a factor for water solubility of chitosan can be reduced in amount. Eventually, there can be fabricated a needle-shaped structure which is sparingly soluble in water, shows high water resistance, can be punctured into the skin without breakage, is able to keep a microscopic form (a microscopic three-dimensional structure on the order of μm) after puncture and places a low burden on a living body.

It will be noted that the resulting needle-shaped structure made of acetylated chitosan should preferably has a degree of acetylation of not less than 35% to not larger than 80%. If the degree of acetylation is less than 35%, there is concern that a difficulty is involved in obtaining a needle-shaped structure which is sparingly soluble in water, shows high water resistance and has at least a projection. On the other hand, when the degree of acetylation of acetylated chitosan exceeds 80%, the reaction time becomes prolong, with concern that productivity lowers. More preferably, the degree of acetylation is from not less than 40% to not larger than 70%.

Third Embodiment

Next, a method for fabricating a needle-shaped structure according to a third embodiment is described in detail.

The needle-shaped structure has a needle-shaped projection and a support substrate supporting the projection as described in the forgoing first embodiment. At least, the projection is formed of a material containing a chitosan. The details of the projection described herein is similar to as described in the first embodiment.

For the fabrication of a needle-shaped structure from a liquid needle-shaped structure material containing a chitosan and an acid, when the needle-shaped structure is subjected to water-resistance treatment after formation thereof, there can be provided a needle-shaped structure which is sparingly soluble in water, shows high water resistance, can be puncture into the skin without breakage, is able to keep a microscopic form (a fine three-dimensional structure on the order of μm) and places a low burden on a living body.

More particularly, when a water-resistance treatment is performed such that a solidified article of needle-shaped structure is formed out of a liquid needle-shape structure material containing a chitosan, a first acid and a second acid and immersed in an aqueous alcohol solution, there can be fabricated a needle-shaped structure which is sparingly soluble in water, shows high water resistance, can be punctured into the skin without breakage, is able to keep a microscopic form after puncture and places a low load on a living body.

At least the projection of the needle-shaped structure fabricated in the third embodiment is sparingly soluble in water. The term "at least the projection of the needle-shaped structure is sparingly soluble in a water solvent" means that "after the needle-shaped structure is immersed in a phosphate buffer physiological saline solution (PBS) with a pH of 7.4 for 24 hours, a reduced volume of at least the projection of the needle-shaped structure is not larger than 5% of the volume prior to the immersion.

The respective steps of the method for fabricating the needle-shaped structure according to the third embodiment are described below in detail.

<Step of Making an Intaglio Plate>

An original plate which determines the form of a needle-shaped structure is made and an intaglio plate whose pattern is inverted relative to the shape of a desired needle-shaped structure is made out of the original plate. This step is similar to as described in the first embodiment.

<Step of Preparing a Liquid Material for Needle-Shaped Structure>

A bioadaptable chitosan is dissolved in an aqueous solution of a first acid and a second acid to prepare a liquid needle-shaped structure material containing a chitosan and these acids. The liquid needle-shaped structure material should preferably have a degree of fluidity sufficient to allow it to flow onto the intaglio plate. In this regard, however, if the prepared needle-shaped structure material has fluidity sufficient to flow onto the intaglio plate, the material may not be liquid, but in a gel form.

The chitosan used may be one as illustrated in the first embodiment.

The first acid is preferably either a tri- or higher valent carboxylic acid or a dicarboxylic acid whose number average molecular weight is not less than 110. The second acid is preferably either a monocarboxylic acid or a dicarboxylic acid whose number average molecular weight is less than 110.

The first and second acids are used to dissolve a chitosan in an aqueous solution thereof. Part of the acids is removed in a subsequent water-resistance step to impart a water resistance to the needle-shaped structure. On this occasion, there are used, as the first acid, a tri- or higher valent carboxylic acid or a dicarboxylic acid whose number average molecular weight is not less than 110 and, as the second acid, a monocarboxylic acid or a dicarboxylic acid whose number average molecular weight is less than 110. This enables the structure not only to have a high water resistance, but also to have needle strength sufficient to permit puncture into the skin and keep the shape of a microscopic needle-shaped structure after puncture into the skin. Additionally, the time required for the step of enhancing the water resistance can be shortened.

The first acid is selected from those acids having such a function as to permit the needle-shaped structure to be insoluble in water and impart satisfactory strength thereto when left in the material in small amounts after the water-resistance treatment. The first acid is preferably chosen from citric acid, tartaric acid, fumaric acid and maleic acid while taking bioadaptability into consideration. Of these, the use of citric acid as the first acid is more preferred.

The second acid is selected from those acids having such a function that the treating time can be shortened over the case where a first acid alone is used in the material at the stage of the water-resistance treatment. When the solidified article made of the needle-shaped structure material is subjected to water-resistance treatment, the second acid used should preferably one that allows dissolution in an alcohol more rapidly than the first acid. The second acid is preferably chosen from formic acid, acetic acid, propionic acid, lactic acid, oxalic acid and malonic acid. Of these, the use of acetic acid as the second acid is more preferred.

If a needle-shaped structure is fabricated using, as an acid, a first acid alone consisting of a tri- or higher valent carboxylic acid or a dicarboxylic acid whose number average molecular weight is at not less than 110, it is possible to obtain a needle-shaped structure having needle strength sufficient to allow puncture into the skin. However, the first acid is more liable to be taken in chitosan, for which an immense amount of time is required for imparting water resistance to the needle-shaped structure in the water-resistance treatment.

On the other hand, where the needle-shaped structure is fabricated using, as an acid, the second acid alone consisting of a monocarboxylic acid or a dicarboxylic acid whose number average molecular weight is less than 110, a time required for imparting a water resistance to the needle-shaped structure in the subsequent water-resistance step can be shortened. However, it does not become possible to obtain a needle-shaped structure having needle strength sufficient to allow puncture into the skin. In addition, the resulting needle-shaped structure undergoes warpage or becomes curved.

The present inventors have found that the combination of the first acid and second acid as an acid enables a needle-shaped structure having satisfactory needle strength to be fabricated within a short time.

The formulation ratios of a chitosan, a first acid and a second acid are appropriately controlled depending on the types of first and second acids from the standpoints that a liquid needle-shaped structure material wherein the chitosan is well dissolved and that the second acid is dissolved out from the solidified article made of a needle-shaped structure material in an alcohol more rapidly than the first acid.

<Step of Filling of a Liquid Needle-Shaped Material>

The liquid needle-shaped structure material is filled onto the intaglio plate. This filling method is similar to as described in the first embodiment.

<Step of Solidifying the Liquid Needle-Shaped Structure Material>

The liquid needle-shaped structure material filled onto the intaglio plate is dried and solidified to obtain a solidified article made of the needle-shaped structure material. This step is similar to as described in the first embodiment.

<Step of Removing the Solidified Article Made of the Needle-Shaped Structure Material>

The solidified article made of the needle-shaped structure material is removed from the intaglio plate. The thus removed solidified article has a final needle-shaped form.

The removing method used may include, for example, a method of physically removing the solidified article from the intaglio plate, a method of chemically, selectively dissolving the intaglio plate, and the like.

<Step of Water-Resistance Treatment of the Solidified Article Made of the Needle-Shaped Structure Material>

The solidified article made of the needle-shaped structure material is subjected to water-resistance treatment. The water-resistance treatment is carried out in such a way that the solidified needle-shaped structure article made of the liquid needle-shaped structure material containing a chitosan and the first and second acids is immersed in an aqueous alcohol solution.

The type of alcohol used for immersion of the solidified article of the needle-shaped structure, the concentration and temperature of the aqueous alcohol solution and the immersion time in the aqueous alcohol solution are, respectively, similar to as described in the first embodiment.

When the solidified article is immersed in an aqueous alcohol solution, a plural-stage treatment is preferably used wherein successive immersions in an aqueous alcohol solution having a high concentration and then in an aqueous alcohol solution with a lower concentration are carried out.

According to the third embodiment adopting the water-resistance treatment, there can be fabricated a needle-shaped structure which is sparingly soluble in water, shows a high water resistance, has satisfactory needle strength, can be punctured into the skin without breakage, is able to keep the microscopic form after puncture and ensures a low burden on a living body.

A bioadaptable chitosan has sparing solubility in water. This needs that for the fabrication of a chitosan needle-shaped structure by use of an intaglio plate, a chitosan be dissolved in an aqueous acid solution to prepare a liquid needle-shaped structure material beforehand. Such a liquid needle-shaped structure material contains not only a chitosan, but also an acid or acids, for which the solidified article having a needle-shaped structure and obtained by drying after formation with an intaglio plate, solidifying and removing from the intaglio plate contains not only a chitosan, but also the acid. The resulting solidified article is poor in water resistance because of the acid being contained. If this is used as a needle-shaped structure as it is, dissolution occurs by contact with moisture or immersion in water. Eventually, not only a high burden is placed on a living body as a result of dissolution in the living body, but also a microscopic form of the needle-shaped structure cannot be kept after puncture.

In the third embodiment, a chitosan is provided as an aqueous solution using an acid and the acid is removed by immersion in an alcohol after formation of a solidified article of needle-shaped structure thereby imparting a water resistance thereto. In this step, the acid used is a combination of a first acid for imparting strength to the needle-shaped structure and a second acid contributing to the shortage of a time for the water-resistance treatment step. This enables the short time fabrication of a needle-shaped structure wherein not only a water resistance is imparted thereto, but also the structure has needle strength sufficient for puncture into the skin and has a microscopic needle kept in its form after puncture.

The needle-shaped structure fabricated according to the third embodiment should preferably contain the first and second acids within a range of not less than 0.5 wt % to not larger than 40 wt % of the needle-shaped structure in total. When the total amount of the acids is set at not larger than 40 wt %, a water resistance can be imparted to the needle-shaped structure. On the other hand, in case where the total of the acids exceeds 40 wt %, it become difficult to make the needle-shaped structure sparingly soluble. In view of rendering the needle-shaped structure resistant to water, a less total amount of the acids contained in the needle-shaped structure is more preferred. However, if the total content of the acids is made less than 0.5%, needle strength becomes small and the needle may be broken or bent, thereby making it difficult to puncture it into the skin.

Example of the invention are described with reference to the accompanying drawings. It will be noted that the needle-shaped structure and the method of fabricating the structure according to the invention should not be construed as limited to the examples.

Example 1

Initially, a silicon substrate was subjected to precision machining to make an original plate wherein projections were formed by arraying 36 square pyramids (height: 150 μm, bottom face: 60 μm×60 μm) at intervals of 1 mm in the form of a lattice of 6 rows and 6 columns. Subsequently, the original plate made out of the silicon substrate was formed thereon with a nickel film in a thickness of 500 μm by a plating method. Thereafter, the original plate was removed by dissolution with an aqueous potassium hydroxide solution heated to 90° C. and having a concentration of 30 wt % to provide an intaglio plate 11 (as shown (a) of FIG. 2) made of nickel.

Separately, chitosan was dissolved in an aqueous citric acid solution to prepare a liquid material for needle-shaped structure. This liquid needle-shaped structure material 12 was placed in a beaker 13 (as shown in (a) of FIG. 2). It will be noted that the liquid needle-shaped structure material 12 had a composition wherein the chitosan and citric acid were dissolved at 5 wt % and 10 wt % relative to water, respectively.

Figure 2:
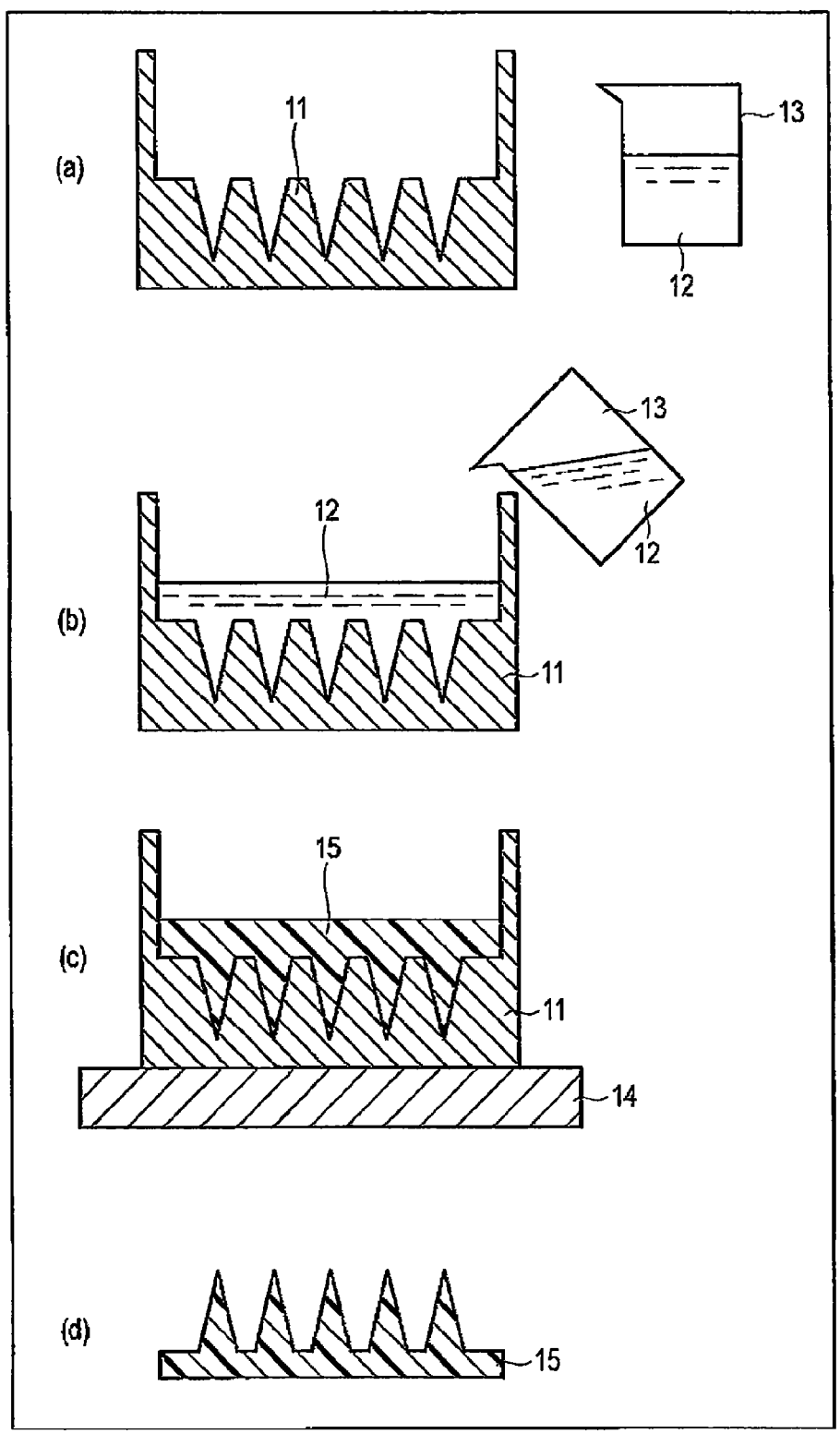
FIG. 2 is a schematic sectional view showing the steps of making a needle-shaped structure in Example 1.

Next, the liquid needle-shaped structure material 12 was filled onto the intaglio plate 11 by use of a spin coating method (a shown in (b) of FIG. 2). The intaglio plate 11 filled with the liquid needle-shaped structure material 12 was heated to 90° C. for 10 minutes by use of a heat source 14 and thus, the needle-shaped structure material 12 was dried and solidified to obtain a solidified article 15 made of the needle-shaped structure material (as shown in (c) of FIG. 2). The heat source used was a hot plate.

Next, the solidified article made of the needle-shaped material was peeled off (removed) from the intaglio plate 11 to obtain a solidified article 15 (as shown in (d) of FIG. 2) made of the needle-shaped structure material.

Figure 3:
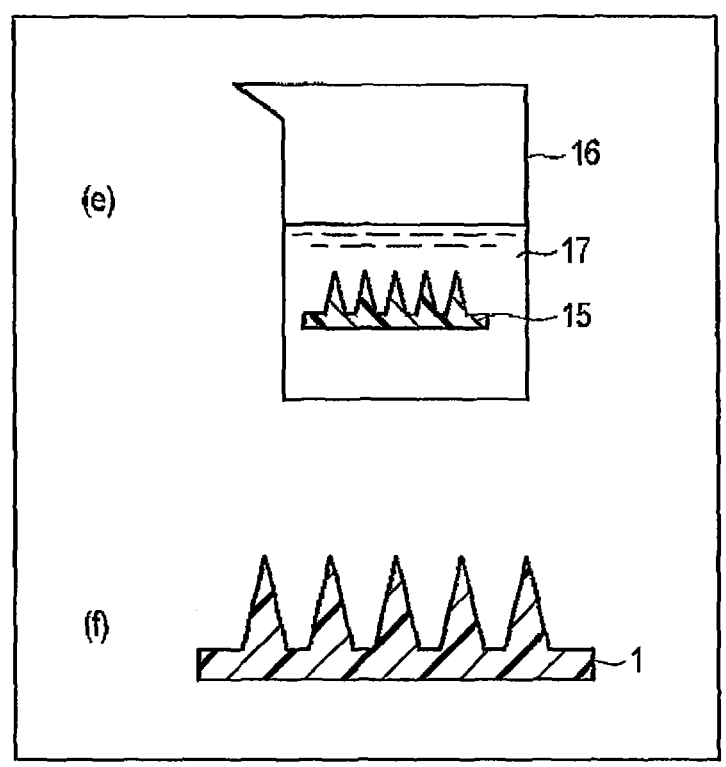
FIG. 3 is a schematic sectional view showing the further steps of making the needle-shaped structure in Example 1.

Next, an aqueous ethanol solution 17 having a concentration of 70 wt % was placed in a beaker 16, and the solidified article 15 made of the needle-shaped structure material was immersed in the aqueous ethanol solution for 18 hours (as shown in (e) of FIG. 2). Thereafter, the solidified article 15 was taken out from the aqueous ethanol solution 17 and naturally dried to obtain a needle-shaped structure 1 shown in (f) of FIG. 3.

Example 2

A needle-shaped structure was made in the same manner as in Example 1 except that there was used, as a liquid needle-shaped structure material, a composition having 5 wt % of chitosan and 10 wt % of citric acid dissolved in water and an aqueous ethanol solution having a concentration of 90 wt % was used.

Example 3

A needle-shaped structure was made in the same manner as in Example 1 except that there was used, as a liquid needle-shaped structure material, a composition having 5 wt % of chitosan and 10 wt % of citric acid dissolved in water and immersion was carried out for 9 hours using an aqueous ethanol solution with a concentration of 70 wt % and then for 9 hours using an aqueous ethanol solution having a concentration of 50%.

Example 4

A needle-shaped structure was made in the same manner as in Example 1 except that there was used, as a liquid needle-shaped structure material, a composition having 5 wt % of chitosan and 10 wt % of citric acid dissolved in water, and an aqueous ethanol solution used as one having a concentration of 70 wt % and heated to 40° C. and the immersion time was set at 8 hours.

Example 5

A needle-shaped structure was made in the same manner as in Example 1 except that there was used, as a liquid needle-shaped structure material, a composition having 5 wt % of chitosan and 6 wt % of citric acid dissolved in water.

Example 6

A needle-shaped structure was made in the same manner as in Example 1 using a similar liquid needle-shaped structure material (with a composition having 5 wt % of chitosan and 10 wt % of citric acid dissolved in water) as in Example 1, except that the resulting solidified article after removal from the intaglio plate was not immersed in an aqueous ethanol solution.

Comparative Example 1

A needle-shaped structure was made in the same manner as in Example 1 except that a composition having 5 wt % of chitosan and 3 wt % of acetic acid dissolved in water was used as a liquid needle-shaped structure material.

Comparative Example 2

A needle-shaped structure was made in the same manner as in Example 1 using a similar liquid needle-shaped structure material as in Example 1 (with a composition having 5 wt % of chitosan and 3 wt % of acetic acid dissolved in water), except that the solidified article obtained after removal from the intaglio plate was not immersed in an aqueous ethanol solution.

The resulting needle-shaped structures of Examples 1-6 and Comparative Examples 1, 2 were subjected to the following evaluations.

<Measurement of an Amount of an Acid in the Needle-Shaped Structure>

Individual needle-shaped structures were dissolved in a 0.5 mol % hydrochloric acid aqueous solution and the resulting solution of the needle-shaped structure was subjected to quantitative analysis with ion chromatography (DX-320, made by Nippon Dionex K.K.) to determine an amount of an acid in the needle-shaped structure.

The results are shown in Table 1.

<Confirmation Test 1>

With respect to the needle-shaped structures obtained in Examples 1-6 and Comparative Examples 1, 2, a confirmation test on insolubilization was performed using a phosphate buffer solution (PBS) with a pH of 7.5. More particularly, each needle-shaped structure was immersed in PBS for 24 hours and sufficiently dried, after which whether the needle-shaped structure was dissolved or not was confirmed with a microscope.

<Confirmation Test 2>

With respect to the needle-shaped structures obtained in Examples 1-6 and Comparative Examples 1, 2, a confirmation test on insolubilization was performed using an artificial skin. More particularly, each needle-shaped structure was punctured into an artificial skin, followed by allowing to stand for 3 hours. Subsequently, the needle-shaped structure was removed from the artificial skin and well dried, followed by confirming whether the needle-shaped structure was dissolved.

<Confirmation Test 3>

The needle-shaped structures obtained in Examples 1-6 and Comparative Examples 1, 2 were visually evaluated with respect to the color tone thereof.

<Confirmation Test 4>

With respect to the needle-shaped structures obtained in Examples 1-6 and Comparative Examples 1, 2, each structure was placed on a flat surface, followed by measurement of a distance of the needle-shaped structure between the flat surface and an uplifted portion thereof by use of a non-contact profile measuring device (YP-21, made by Sony Corporation). The structure whose uplift length was less than 1 mm was evaluated as "not warped", a structure whose uplift length was at larger than 1 mm to less than 2 mm was as "partially warped" and a structure whose uplift length was at not less than 2 mm was as "significantly warped". Those "significantly warped" structures whose uplift length was at not less than 2 mm could be judged as not used for product because of their low puncture performance.

The test conditions of Examples 1-6 and Comparative Examples 1, 2 are shown in the following Table 1, and the results of the tests are shown in the following Table 2.

TABLE 1

|  | Composition of liquid needle-shaped structure material (ratio by weight) | Concentration of an aqueous ethanol solution and immersion time | Amount of an acid in needle-shaped structure (wt %) |
|---|---|---|---|
| Example 1 | chitosan:citric acid = 5:10 | 70 wt %/18 hours | 32.0 |
| Example 2 | chitosan:citric acid = 5:10 | 90 wt %/18 hours | 38.0 |
| Example 3 | chitosan:citric acid = 5:10 | (1) 70 wt %/9 hours (2) 50 wt %/9 hours | 0.5 |
| Example 4 | chitosan:citric acid = 5:10 | 70 wt %/8 hours 40° C. | 30.0 |
| Example 5 | chitosan:citric acid = 5:6 | 70 wt %/18 hours | 33.0 |
| Example 6 | chitosan:citric acid = 5:10 | no immersion | 66.6 |
| Comp. Ex. 1 | chitosan:citric acid = 5:3 | 70 wt %/18 hours | — |
| Comp. Ex. 2 | chitosan:citric acid = 5:3 | no immersion | 37.5 |

TABLE 2

|  | Confirmation Test 1 | Confirmation Test 2 | Confirmation Test 3 | Confirmation Test 4 |
|---|---|---|---|---|
| Example 1 | insoluble | insoluble | white | not warped |
| Example 2 | insoluble | insoluble | Light white | not warped |
| Example 3 | insoluble | insoluble | white | not warped |
| Example 4 | insoluble | insoluble | white | not warped |
| Example 5 | insoluble | insoluble | light yellow, transparent | not warped |
| Example 6 | dissolved without leaving shape | projections and support substrate partially dissolved | yellow, transparent | partially warped |
| Comp. Ex. 1 | insoluble | dissolved | yellow, transparent | significantly warped |
| Comp. Ex. 2 | dissolved without leaving shape | projections and support substrate partially dissolved | yellow, transparent | significantly warped |

As will be apparent from Tables 1, 2, the needle-shaped structures of Examples 1-5 which are made by immersion in the aqueous ethanol solution after formation by dissolution of chitosan in an aqueous acid solution are not dissolved in PBS in the confirmation test 1. In contrast thereto, with the needle-shaped structure of Example 6 made without immersion in an aqueous acid solution after formation by dissolution of chitosan in an aqueous acid solution is dissolved out in PBS of the confirmation test 1, thereby not enabling the needle-shaped form of the projections to be kept.

It will be noted that with respect to the needle-shaped structures of Examples 1-5, their volumes prior to immersion in a phosphate buffer solution (PBS) with a pH of 7.5 for 24 hours and a volume after the immersion over 24 hours were, respectively, measured. As a result, it was found that reduced volumes of the respective needle-shaped structures were all at not larger than 5% relative to the volumes prior to the immersion.

As will be seen from Table 1, it was confirmed that the needle-shaped structures of Examples 1-5 were not dissolved in the artificial skin in the confirmation test 2. In contrast thereto, the needle-shaped structure of Example 6 was dissolved in the artificial skin, thereby not keeping the needle-shaped form of the projections. In this regard, however, the needle-shaped structures of Examples 1-6 were all good with respect to the puncture into the skin.

Further, the needle-shaped structures of Examples 1-4 were light white-white in color tone and was thus excellent in cleanliness.

Moreover, the respective needle-shaped structures of Examples 1-5 were punctured into the artificial skin and the volumes of the structures prior to and after standing for 3 hours were measured. As a result, the reduced volumes of the respective needle-shaped structures obtained after the puncture and standing for 3 hours were all at not larger than 5% of the volumes prior to the puncture and standing.

In the following Examples 7-21, the temperature of aqueous ethanol solutions was set at 20° C. unless otherwise indicated.

Example 7

Initially, a silicon substrate was subjected to precision machining to make an original plate wherein projections were formed by arraying 36 square pyramids (height: 150 μm, bottom face: 60 μm×60 μm) at intervals of 1 mm in the form of a lattice of 6 rows and 6 columns. Subsequently, the original plate made out of the silicon substrate was formed thereon with a nickel film in a thickness of 500 μm by a plating method. Thereafter, the original plate was removed by dissolution with an aqueous potassium hydroxide solution heated to 90° C. and having a concentration of 30 wt % to provide an intaglio plate 21 made of nickel.

Separately, chitosan was dissolved in an aqueous citric acid solution with a concentration of 5 wt % to prepare a liquid material for needle-shaped structure. This liquid needle-shaped structure material 22 was placed in a beaker 23 (as shown in (b) of FIG. 4). It will be noted that the liquid needle-shaped structure material 12 had a composition wherein 5 wt % of chitosan and 10 wt % of citric acid relative to water were dissolved.

Figure 4:
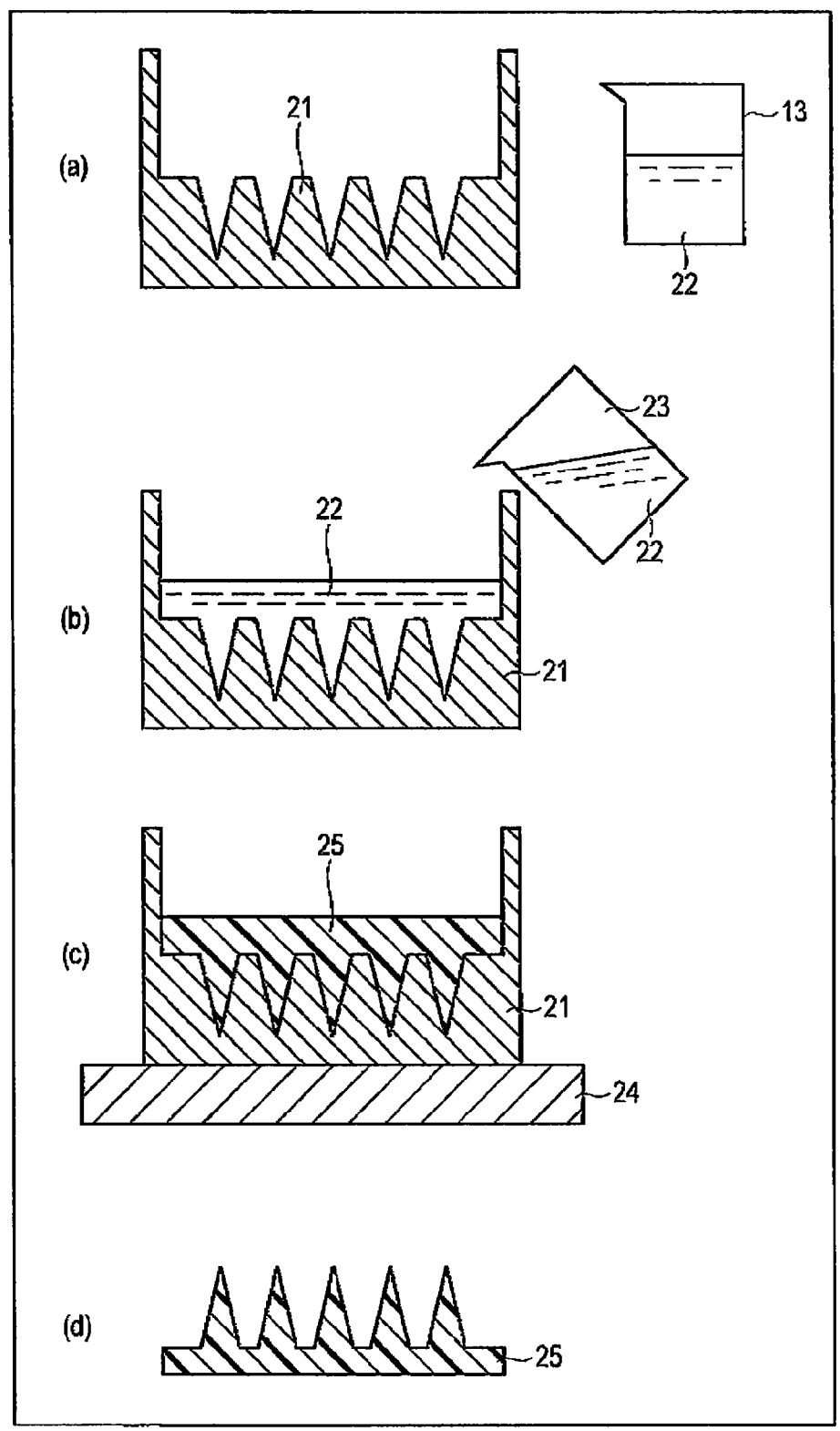
FIG. 4 is a schematic sectional view showing the steps of making a needle-shaped structure in Example 7.

Next, the liquid needle-shaped structure material 22 was filled onto the intaglio plate 21 by use of a spin coating method (a shown in (b) of FIG. 4). The intaglio plate 21 filled with the liquid needle-shaped structure material 22 was heated to 90° C. for 10 minutes by use of a heat source 24 and thus, the needle-shaped structure material 22 was dried and solidified to obtain a solidified article 25 made of the needle-shaped structure material (as shown in (c) of FIG. 4). The heat source 24 used was a hot plate.

Next, the solidified article 25 made of the needle-shaped material was peeled off (removed) from the intaglio plate 21 to obtain a solidified article 25 (as shown in (d) of FIG. 4) made of the needle-shaped structure material.

Figure 5:
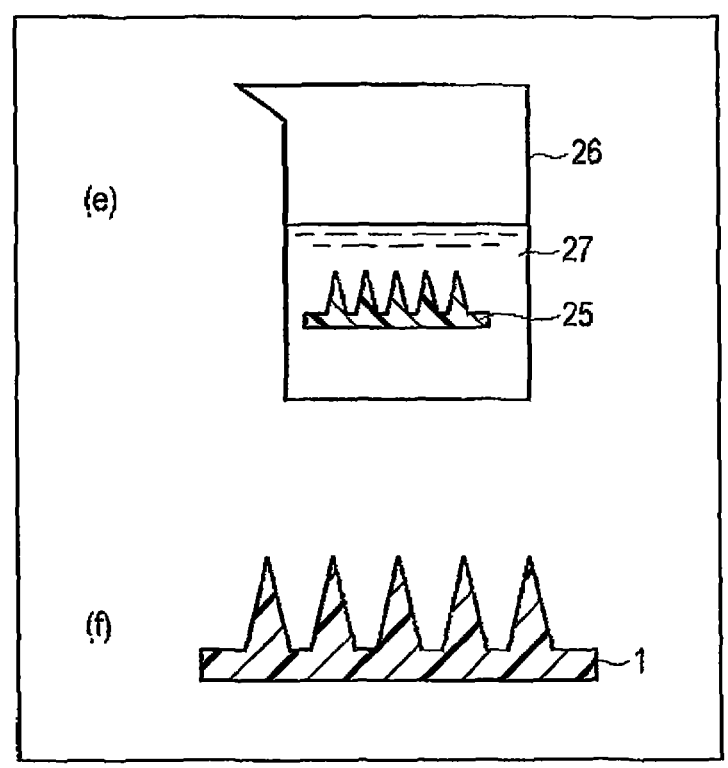
FIG. 5 is a schematic sectional view showing the further steps of making the needle-shaped structure in Example 7.

Next, an aqueous ethanol solution 27 having a concentration of 90 wt % was placed in a beaker 26, and the solidified article 25 made of the needle-shaped structure material was immersed in the aqueous ethanol solution 27 for 18 hours (as shown in (e) of FIG. 5). Thereafter, the solidified article 25 was taken out from the aqueous ethanol solution 27 and naturally dried to obtain a needle-shaped structure 1 shown in (f) of FIG. 5.

Example 8

A needle-shaped structure was made in the same manner as in Example 7 except that in the step of immersion in the aqueous ethanol solution, the solidified article 25 made of the needle-shaped structure material was immersed in an aqueous ethanol solution with a concentration of 80 wt % for 18 hours.

Example 9

A needle-shaped structure was made in the same manner as in Example 7 except that in the step of immersion in the aqueous ethanol solution, the solidified article 25 made of the needle-shaped structure material was immersed in an aqueous ethanol solution with a concentration of 70 wt % for 16 hours.

Example 10

A needle-shaped structure was made in the same manner as in Example 7 except that in the step of immersion in the aqueous ethanol solution, the solidified article 25 made of the needle-shaped structure material was immersed in an aqueous ethanol solution with a concentration of 60 wt % for 16 hours.

Example 11

A needle-shaped structure was made in the same manner as in Example 7 except that in the step of immersion in the aqueous ethanol solution, the solidified article 25 made of the needle-shaped structure material was immersed in an aqueous ethanol solution, heated to 50° C. and having a concentration of 80 wt %, for 10 hours.

Example 12

A needle-shaped structure was made in the same manner as in Example 7 except that in the step of immersion in the aqueous ethanol solution, the solidified article 25 made of the needle-shaped structure material was immersed in an aqueous ethanol solution with a concentration of 80 wt % for 5 hours and subsequently in an aqueous ethanol solution with a concentration of 60 wt % for 5 hours.

Comparative Example 3

A needle-shaped structure was made in the same manner as in Example 7 using a similar liquid needle-shaped structure material (with a composition dissolving 5 wt % of chitosan and 7 wt % of citric acid relative to water) as used in Example 7, except that a solidified article after removal from the intaglio plate was not immersed in an aqueous ethanol solution.

Example 13

Initially, a silicon substrate was subjected to precision machining to make an original plate wherein projections were formed by arraying 36 square pyramids (height: 150 μm, bottom face: 60 μm×60 μm) at intervals of 1 mm in the form of a lattice of 6 rows and 6 columns. Subsequently, the original plate made out of the silicon substrate was formed thereon with a nickel film in a thickness of 500 μm by a plating method. Thereafter, the original plate was removed by dissolution with an aqueous potassium hydroxide solution heated to 90° C. and having a concentration of 30 wt % to provide an intaglio plate made of nickel.

Separately, chitosan was dissolved in an aqueous acetic acid solution with a concentration of 5 wt % to prepare a liquid material for needle-shaped structure. This liquid needle-shaped structure material was placed in a beaker. It will be noted that the liquid needle-shaped structure material had a composition wherein 5 wt % of chitosan and 2.5 wt % of citric acid relative to water were dissolved.

Next, the liquid needle-shaped structure material was filled onto the intaglio plate by use of a spin coating method. The intaglio plate filled with the liquid needle-shaped structure material was heated to 90° C. for 10 minutes by use of a heat source to dry and solidify the needle-shaped structure material thereby obtaining a solidified article made of the needle-shaped structure material. The heat source used was a hot plate.

Next, the solidified article made of the needle-shaped material was peeled off (removed) from the intaglio plate to obtain the solidified article made of the needle-shaped structure material.

Next, a mixed solution of 5 g of acetic anhydride and 40 g of methanol was placed in a beaker, and the solidified article made of the needle-shaped structure material was immersed in the mixed solution for 2 days. Subsequently, the solidified article was taken out from the mixed solution and immersed in methanol in a beaker for 1 day. Thereafter, the solidified article removed from the methanol was naturally dried to obtain a needle-shaped structure.

Example 14

A needle-shaped structure was made in the same manner as in Example 13 except that the time for immersion in the mixed solution of 5 g of acetic anhydride and 40 g of methanol was set at one day.

Comparative Example 4

A needle-shaped structure was made in the same manner as in Example 13 except that the solidified article made of the needle-shaped structure material was not immersed in the mixed solution of 5 g of acetic anhydride and 40 g of methanol and then in methanol.

With respect to the needle-shaped structures obtained in Example 7-14, volumes prior to immersion in a phosphate buffer solution (PBS) with a pH of 7.5 for 24 hours and after the immersion for 24 hours were measured, respectively. As a result, reduced volumes of the respective needle-shaped structures after the immersion were all not larger than 5% of the volumes prior to the immersion.

The needle-shaped structures obtained in Examples 7-14 and Comparative Examples, 3, 4 were subjected to the foregoing confirmation tests 1, 2. The results are shown in the following Table 3.

TABLE 3

|  | Confirmation Test 1 | Confirmation Test 2 |
| --- | --- | --- |
| Example 7 | insoluble | insoluble |
| Example 8 | insoluble | insoluble |
| Example 9 | insoluble | insoluble |
| Example 10 | insoluble | insoluble |
| Example 11 | insoluble | insoluble |
| Example 12 | insoluble | insoluble |
| Comp. Ex. 3 | dissolved without leaving shape | projections and support substrate partially dissolved |
| Example 13 | insoluble | Insoluble |
| Example 14 | insoluble | insoluble |
| Comp. Ex. 4 | dissolved without leaving shape | projections and support substrate partially dissolved |

As will be apparent from the above Table 3, it was confirmed that the needle-shaped structures of Example 7-14 were not dissolved in the artificial skin of the confirmation test 2. In contrast thereto, the needle-shaped structure of Comparative Example 3 was dissolved in the artificial skin and the shape of the needle-shaped projections could not be kept.

With respect to the needle-shaped structures of Examples 7-12, volumes of the needle-shaped structures prior to puncture into an artificial skin and standing for 3 hours and volumes after standing for 3 hours were measured, respectively. As a result, it was found that the reduced volumes of the respective needle-shaped structures after standing for 3 hours were all at not larger than 5% of the volumes after the puncture but prior to the standing.

The needle-shaped structures obtained in Examples 13, 14 and Comparative Example 4 were each subjected to measurement of a degree of acetylation according to colloidal titration. The colloidal titration was carried out using a toluidine blue solution as an indicator and a potassium polyvinyl sulfate solution was used for titration. The needle-shaped structures of Examples 13, 14, respectively, had degrees of acetylation of 38% and 78% and were found not to be dissolved in PBS in the confirmation test 1. On the other hand, the needle-shaped structure of Comparative Example 4 made without immersion in a mixed solution of acetic anhydride and methanol and then in methanol after formation by dissolution of chitosan in the aqueous acid solution had a degree of acetylation of 16% and was dissolved in PBS in the confirmation test 1 thereby not keeping the shape of the needle-shaped projections.

Example 15

Initially, a silicon substrate was subjected to precision machining to make an original plate wherein projections were formed by arraying 36 square pyramids (height: 150 μm, bottom face: 60 μm×60 μm) at intervals of 1 mm in the form of a lattice of 6 rows and 6 columns. Subsequently, the original plate made out of the silicon substrate was formed thereon with a nickel film in a thickness of 500 μm by a plating method. Thereafter, the original plate was removed by dissolution with an aqueous potassium hydroxide solution heated to 90° C. and having a concentration of 30 wt % to provide an intaglio plate 31 made of nickel (as in (a) of FIG. 6).

Separately, chitosan was dissolved in an aqueous mixed solution of 2.04 wt % of citric acid and 1.27 wt % of acetic acid to prepare a liquid material for needle-shaped structure. This liquid needle-shaped structure material 32 was placed in a beaker 33 (as shown in (a) of FIG. 6). It will be noted that the liquid needle-shaped structure material had a composition of dissolving 2.48 wt % of chitosan, 1.99 wt % of citric acid and 1.24 wt % of acetic acid relative to water.

Figure 6:
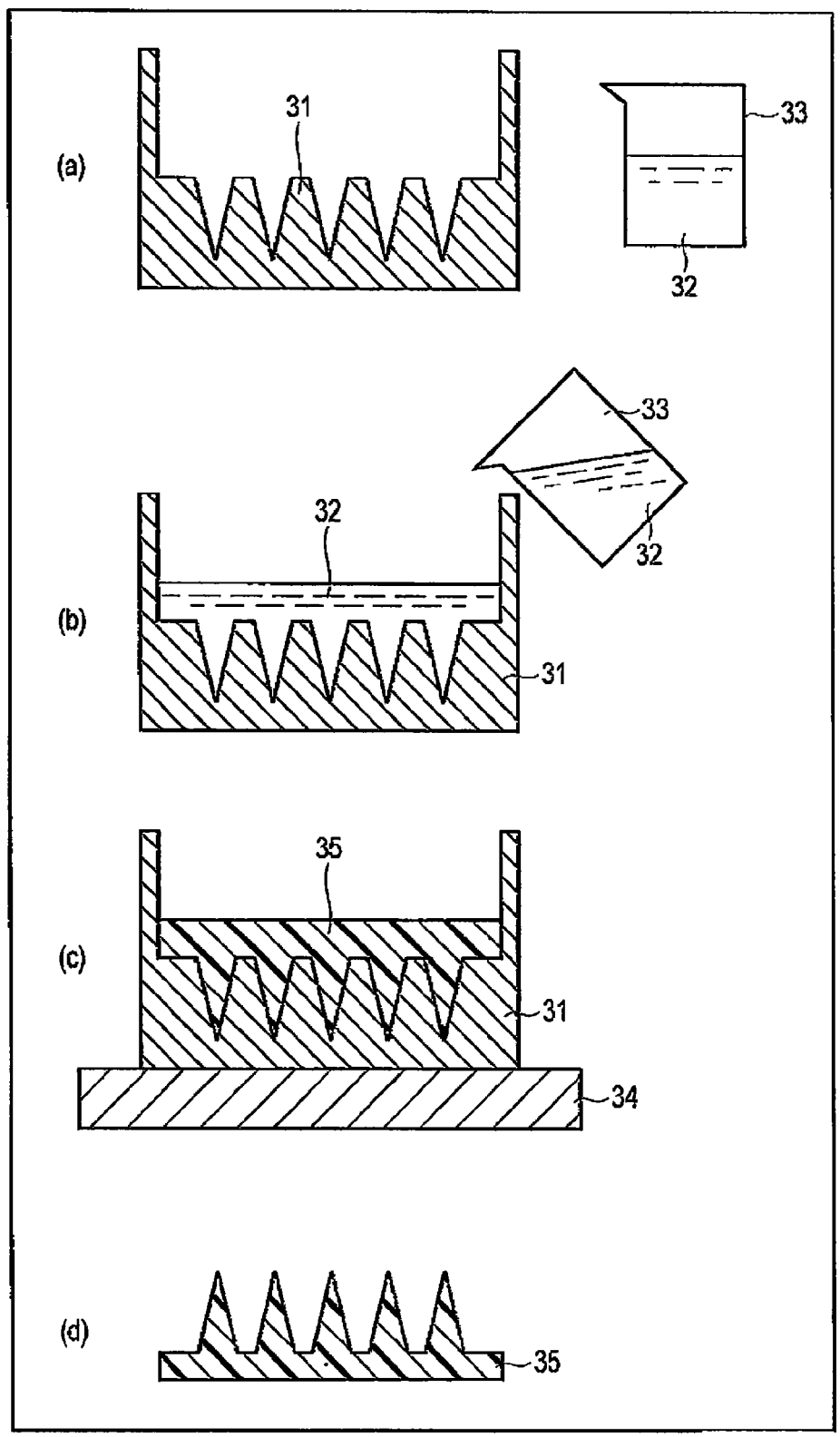
FIG. 6 is a schematic sectional view showing the steps of making a needle-shaped structure in Example 15.

Next, the liquid needle-shaped structure material was filled onto the intaglio plate 31 by use of a spin coating method (as shown in (b) of FIG. 6). Subsequently, the intaglio plate 31 filled with the liquid needle-shaped structure material 32 was allowed to stand, for example, on a thermal conductive support plate 34 made of a metal for 48 hours, followed by natural drying and solidification of the needle-shaped structure material to obtain a solidified article 35 made of the needle-shaped structure material (as shown in (c) of FIG. 6).

Next, the solidified article 35 made of the needle-shaped material was peeled off (removed) from the intaglio plate 31 to obtain the solidified article 35 made of the needle-shaped structure material (as shown in (d) of FIG. 6).

Figure 7:
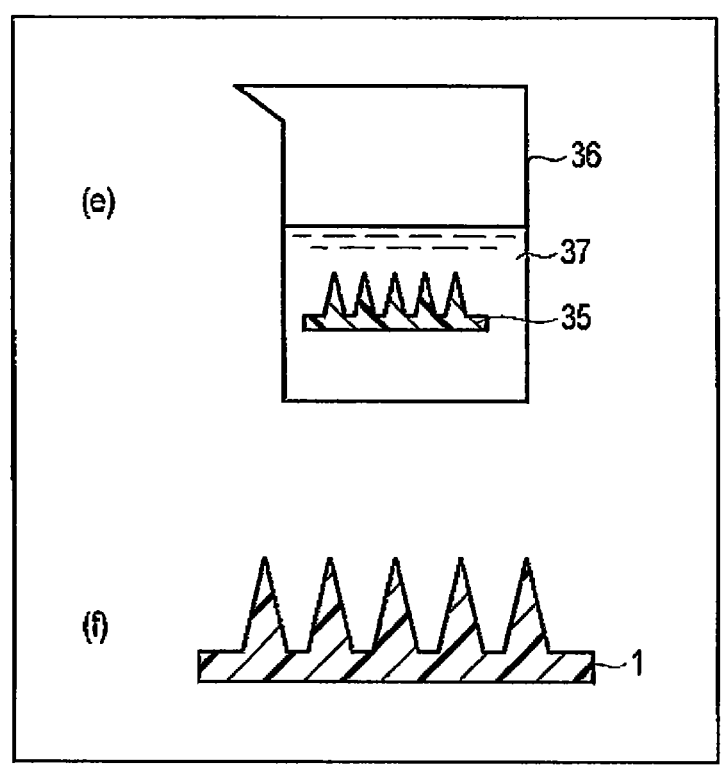
FIG. 7 is a schematic sectional view showing the further steps of making the needle-shaped structure in Example 15.

Next, an aqueous ethanol solution 37 with a concentration of 70 wt % was placed in a beaker 36, in which the solidified article 35 made of the needle-shaped structure material was immersed for 16 hours (as shown in (e) of FIG. 7). Thereafter, the solidified article 35 was taken out from the aqueous ethanol solution 37 and naturally dried to obtain a needle-shaped structure 1 shown in (f) of FIG. 7.

Example 16

A needle-shaped structure was made in the same manner as in Example 15 except that in the step of preparing a liquid needle-shaped structure material, chitosan was dissolved in an aqueous mixed acid solution of 2.05 wt % of citric acid and 0.64 wt % of acetic acid so as to provide a composition wherein 2.50 wt % of chitosan, 2.00 wt % of citric acid and 0.62 wt % of acetic acid were dissolved relative to water.

Example 17

A needle-shaped structure was made in the same manner as in Example 15 except that in the step of preparing a liquid needle-shaped structure material, chitosan was dissolved in an aqueous mixed acid solution of 2.31 wt % of citric acid and 0.26 wt % of acetic acid so as to provide a composition wherein 2.50 wt % of chitosan, 2.25 wt % of citric acid and 0.25 wt % of acetic acid were dissolved relative to water.

Example 18

A needle-shaped structure was made in the same manner as in Example 15 except that in the step of preparing a liquid needle-shaped structure material, chitosan was dissolved in an aqueous mixed acid solution of 2.05 wt % of citric acid and 0.64 wt % of formic acid so as to provide a composition wherein 2.50 wt % of chitosan, 2.00 wt % of citric acid and 0.62 wt % of formic acid were dissolved relative to water.

Example 19

A needle-shaped structure was made in the same manner as in Example 15 except that in the step of preparing a liquid needle-shaped structure material, chitosan was dissolved in an aqueous mixed acid solution of 2.31 wt % of citric acid and 0.26 wt % of formic acid so as to provide a composition wherein 2.5 wt % of chitosan, 2.25 wt % of citric acid and 0.25 wt % of formic acid were dissolved relative to water.

Example 20

A needle-shaped structure was made in the same manner as in Example 15 except that in the step of preparing a liquid needle-shaped structure material, chitosan was dissolved in an aqueous mixed acid solution of 2.05 wt % of citric acid and 0.64 wt % of acetic acid so as to provide a composition wherein 2.50 wt % of chitosan, 2.00 wt % of citric acid and 0.62 wt % of acetic acid were dissolved relative to water and that the immersion time of the solidified article 35 made of the needle-shaped structure material was set at 8 hours.

Example 21

A needle-shaped structure was made in the same manner as in Example 15 except that in the step of preparing a liquid needle-shaped structure material, chitosan was dissolved in an aqueous mixed acid solution of 2.05 wt % of citric acid and 0.64 wt % of formic acid so as to provide a composition wherein 2.50 wt % of chitosan, 2.00 wt % of citric acid and 0.62 wt % of formic acid were dissolved relative to water and that the immersion time of the solidified article 35 made of the needle-shaped structure material was set at 8 hours.

Comparative Example 5

A needle-shaped structure was made in the same manner as in Example 15 except that in the step of preparing a liquid needle-shaped structure material, chitosan was dissolved in an aqueous acid solution of 3.18 wt % of citric acid so as to provide a composition wherein 2.48 wt % of chitosan and 3.11 wt % of citric acid were dissolved relative to water.

Comparative Example 6

A needle-shaped structure was made in the same manner as in Example 15 except that in the step of preparing a liquid needle-shaped structure material, chitosan was dissolved in an aqueous acid solution of 3.18 wt % of citric acid so as to provide a composition wherein 2.48 wt % of chitosan and 3.11 wt % of citric acid were dissolved relative to water and that the immersion time of the solidified article 35 made of the needle-shaped structure material was set at 96 hours.

Comparative Example 7

A needle-shaped structure was made in the same manner as in Example 15 except that in the step of preparing a liquid needle-shaped structure material, chitosan was dissolved in an aqueous acid solution of 3.18 wt % of citric acid so as to provide a composition wherein 2.48 wt % of chitosan and 3.11 wt % of citric acid were dissolved relative to water and that the immersion time of the solidified article 35 made of the needle-shaped structure material was set at 120 hours.

Comparative Example 8

A needle-shaped structure was made in the same manner as in Example 15 except that in the step of preparing a liquid needle-shaped structure material, chitosan was dissolved in an aqueous solution of 1.30 wt % of acetic acid so as to provide a composition wherein 2.53 wt % of chitosan and 1.27 wt % of acetic acid were dissolved relative to water and that the immersion time of the solidified article 35 made of the needle-shaped structure material was set at 8 hours.

Comparative Example 9

A needle-shaped structure was made in the same manner as in Example 15 except that in the step of preparing a liquid needle-shaped structure material, chitosan was dissolved in an aqueous mixed acid solution of 2.04 wt % of citric acid and 1.27 wt % of tartaric acid so as to provide a composition wherein 2.48 wt % of chitosan, 1.99 wt % of citric acid and 1.24 wt % of tartaric acid were dissolved relative to water.

The needle-shaped structures obtained in Examples 15-21 and Comparative Examples 5-9 were subjected to the following confirmation tests.

<Confirmation Test 5>

With respect to the needles-shaped structures obtained in Examples 15-21 and Comparative Examples 5-9, the confirmation test on needle formation was carried out. More particularly, each needle-shaped structure was observed with a microscope to confirm the presence or absence of bentness, torsion, shrinkage and breakage.

<Confirmation Test 6>

The needles-shaped structures obtained in Examples 15-21 and Comparative Examples 5-9 were subjected to a confirmation test on discoloration and unevenness of the needles and substrate. Moe particularly, the needle-shaped structure was visually observed to confirm the presence or absence of the discoloration and unevenness of the needles and substrate thereof.

<Confirmation Test 7>

The needle-shaped structures obtained in Examples 15-21 and Comparative Examples 5-9 were subjected to a confirmation test on needle strength. More particularly, a force was applied from a side face of a needle-shaped structure by use of a blade having a similar size as the needle-shaped structure and a breakage force was measured. One whose measurement was at not less than 7.0 gw was accepted as passed. On the other hand, one whose measurement was less than 7.0 gw was accepted as rejected.

<Confirmation Test 8>

The needle-shaped structures obtained in Examples 15-21 and Comparative Examples 5-9 were subjected to a confirmation test on needle strength. More particularly, the needle-shaped structure was immersed in pure water for 30 minutes and removed from the pure water, and well dried, followed by confirming through a microscope whether or not the needle-shaped structure was dissolved. On this occasion, one which was not confirmed as dissolved was judged as "not dissolved", one wherein not less than 1% of the needles among plural needles was dissolved was as "partially dissolved", and one wherein needles disappeared was as "dissolved".

The test conditions of Examples 15-21 and Comparative Examples 5-9 are shown in the following Table 4 and the test results are shown in the following Table 5.

It will be noted that with respect to the needle-shaped structures obtained in Examples 15, 16 and 17, the acid content was determined according to the following method.

First and second acids in a needle-shaped structure was quantitatively determined by completely dissolving the needle-shaped structure in an aqueous 0.5% HCl solution, subjecting a 1000-fold diluted solution thereof to measurement with ion chromatography, and multiply the resulting value by 1000.

The needle-shaped structure of Example 15 was such that the content of the first acid (citric acid) relative to the needle-shaped structure was at 25 wt % and the content of the second acid was at 0.15 wt %.

The needle-shaped structure of Example 16 was such that the content of the first acid (citric acid) relative to the needle-shaped structure was at 26 wt % and the content of the second acid was at 0.07 wt %.

The needle-shaped structure of Example 17 was such that the content of the first acid (citric acid) relative to the needle-shaped structure was at 31 wt % and the content of the second acid was at 0.02 wt %.

As to the needle-shaped structures of Examples 15-17, volumes thereof prior to immersion in a phosphate buffer saline solution (PBS) with a pH of 7.4 and after the immersion for 24 hours were measured, respectively. As a result, it was found that reduced volumes of the respective needle-shaped structures after the immersion were at not larger than 5% of those volumes prior to the immersion, respectively.

TABLE 4

|  | Chitosan (amount) | First acid (amount) | Second acid (amount) | Immersion time in alcohol |
|---|---|---|---|---|
| Example 15 | chitosan (2.48 wt %) | citric acid (1.99 wt %) | acetic acid (1.24 wt %) | 16 hours |
| Example 16 | chitosan (2.50 wt %) | citric acid (2.00 wt %) | acetic acid (0.62 wt %) | 16 hours |
| Example 17 | chitosan (2.50 wt %) | citric acid (2.25 wt %) | acetic acid (0.25 wt %) | 16 hours |
| Example 18 | chitosan (2.50 wt %) | citric acid (2.00 wt %) | formic acid (0.62 wt %) | 16 hours |
| Example 19 | chitosan (2.50 wt %) | citric acid (2.25 wt %) | formic acid (0.25 wt %) | 16 hours |
| Example 20 | chitosan (2.50 wt %) | citric acid (2.00 wt %) | acetic acid (0.62 wt %) | 8 hours |
| Example 21 | chitosan (2.50 wt %) | citric acid (2.00 wt %) | formic acid (0.62 wt %) | 8 hours |
| Comp. Ex. 5 | chitosan (2.48 wt %) | citric acid (3.11 wt %) | — | 16 hours |
| Comp. Ex. 6 | chitosan (2.48 wt %) | citric acid (3.11 wt %) | — | 96 hours |
| Comp. Ex. 7 | chitosan (2.48 wt %) | citric acid (3.11 wt %) | — | 120 hours |
| Comp. Ex. 8 | chitosan (2.53 wt %) | — | acetic acid (1.57 wt %) | 16 hours |
| Comp. Ex. 9 | chitosan (2.53 wt %) | citric acid (1.99 wt %) tartaric acid (1.24%) | — | 16 hours |

TABLE 5

|  | Confirmation Test 5 | Confirmation Test 6 | Confirmation Test 7 | Confirmation Test 8 |
|---|---|---|---|---|
| Example 15 | needle shape kept | substantially transparent, free of unevenness | pass | not dissolved |

TABLE 5-continued

|  | Confirmation Test 5 | Confirmation Test 6 | Confirmation Test 7 | Confirmation Test 8 |
|---|---|---|---|---|
| Example 16 | needle shape kept | substantially transparent, free of unevenness | pass | not dissolved |
| Example 17 | needle shape kept | substantially transparent, free of unevenness | pass | not dissolved |
| Example 18 | needle shape kept | substantially transparent, free of unevenness | pass | not dissolved |
| Example 19 | needle shape kept | substantially transparent, free of unevenness | pass | not dissolved |
| Example 20 | needle shape kept | substantially transparent, free of unevenness | pass | dissolved |
| Example 21 | needle shape kept | substantially transparent, free of unevenness | pass | dissolved |
| Comp. Ex. 5 | needle shape kept | substantially transparent, free of unevenness | pass | dissolved |
| Comp. Ex. 6 | needle shape kept | substantially transparent, free of unevenness | pass | partially dissolved |
| Comp. Ex. 7 | needle shape kept | substantially transparent, free of unevenness | pass | not dissolved |
| Comp. Ex. 8 | warped due to the shrinkage of substrate | semi-transparent brown, free of unevenness | rejection | not dissolved |
| Comp. Ex. 9 | needle-shaped structure curved | milky white, uneven | pass | dissolved |

In view of the results of the above Tables 4, 5, it has been found that the needle-shaped structures (Examples 15-21) are fairly high in water resistance, have needle strength sufficient to be punctured into the skin, and are able to keep the microscopic shape of the needle-shaped structures after puncture and that a time required for the step of enhancing the water resistance can be set at 16 hours.

In contrast, although the needle-shaped structures (Comparative Examples 5-7, 9) show satisfactory water resistance and needle strength, an enormous amount of time is required for the step of enhancing the water resistance. With the needle-shaped structure (Comparative Example 8) free of a first acid, it has been confirmed that satisfactory needle strength cannot be imparted thereto and warpage is observed due to the shrinkage of the substrate.

Needle-shaped structure is usable in various fields where a microscopic needle-shaped structure is desired. The material for the needle-shaped structure is favorably one which does not adversely influence a human body if the needle-shaped structure is broken and remains in the human body. For this purpose, International Publication Pamphlet No. 2008/020632 describes the use of bioadaptable materials such as chitin, chitosan and the like as a needle-shaped structure material.

Chitin is a component contained in the shell of crustacean such as a crab, a shrimp or the like and chitosan is a deacetylated product thereof. Although there is no clear boundary difference between chitin and chitosan, common practice is such that those obtained by deacetylation of chitin at not less than 70% are called chitosan.

A desirable needle-shaped structure is one that exhibits solubility or non-solubility inside a living body depending on its use related to a drug to be delivered and also to a prescription against symptoms. The structure preferably has high bioadaptability irrespective of whether it is soluble or non-soluble.

One aspect of the invention provides a needle-shaped structure which is made of a chitosan possessing high bioadaptability and is low in burden on the living body.

Another aspect of the invention provides a method for fabricating a needle-shaped structure which is high in water resistance and is able to keep its microscopic shape even after puncture into the skin and thus has a low body burden.

Yet another aspect of the invention provides a method for fabricating a needle-shaped structure wherein there is shortened a time required for the step of enhancing a water resistance among the steps of fabricating the needle-shaped structure which is high in water resistance, is low in body burden and is able to keep its microscopic shape after puncture into the skin.

According to a first embodiment of the invention, there is provided a needle-shaped structure which includes a needle-shaped projection and a support substrate supporting the projection, the projection at least containing a chitosan and citric acid.

According to a second embodiment of the invention, there is provided a method for fabricating a needle-shaped structure having a needle-shaped projection and a support substrate supporting the projection, the method including the steps of:

(a) providing an intaglio plate having a needle-shaped recess;

(b) repairing a liquid material for needle structure containing a chitosan and an acid;

(c) filling the liquid material for needle-shaped structure onto the intaglio plate;

(d) drying the liquid material for needle-shaped structure filled onto the intaglio plate to solidify the liquid, needle-shaped structure material thereby obtaining a solidified article made of the needle-shaped structure material;

(e) removing the solidified article made of the needle-shaped structure material from the intaglio plate; and (f) immersing the thus removed solidified article made of the needle-shaped structure material in an aqueous alcohol solution.

According to a third embodiment of the invention, there is provided a method for fabricating a needle-shaped structure having a needle-shaped projection and a support substrate supporting the needle-shaped projection, the method including the steps of:

(a) providing an intaglio plate having a needle-shaped recess;

(b) preparing a liquid material for needle-shaped structure containing a chitosan and an acid;

(c) filling the liquid material for needle-shaped structure onto the intaglio plate;

(d) drying the liquid material for needle-shaped structure filled onto the intaglio plate to obtain a solidified article made of a needle-shaped structure material;

(e) removing the solidified article made of the needle-shaped structure material from the intaglio plate; and (f) acetylating the chitosan in the solidified article made of the needle-shaped structure material.

According to a fourth embodiment of the invention, there is provided a method for fabricating a needle-shaped structure having a needle-shaped projection and a support substrate supporting the projection, the method including the steps of:

(a) providing an intaglio plate having a needle-shaped recess;

(b) preparing a liquid material for needle-shaped structure containing a chitosan, a first acid and a second acid;

(c) filling the liquid material for needle-shaped structure onto the intaglio plate;

(d) drying the liquid material for needle-shaped structure filled onto the intaglio plate to solidify the liquid needle-shaped structure material thereby obtaining a solidified article made of the needle-shaped structure material;

(e) removing the solidified article made of the needle-shaped structure material from the intaglio plate; and (f) immersing the thus removed solidified article made of the needle-shaped structure material in an aqueous alcohol solution, wherein the first acid is made of a tri- or higher valent carboxylic acid or a dicarboxylic acid whose number average molecular weight is not less than 110, and the second acid is made of a monocarboxylic acid or a dicarboxylic acid whose number average molecular weight is less than 110.

INDUSTRIAL APPLICABILITY

As having stated hereinabove, the needle-shaped structure of the embodiments is usable in various fields demanding a microscopic needle-shaped structure. For instance, there can be expected applications, as a needle-shaped structure, to MEMS devices, optical members, sampling tools, drug developments, medical use, cosmetics, beauty cares and the like.

Obviously, numerous modifications and variations of the present invention are possible in light of the above teachings. It is therefore to be understood that within the scope of the appended claims, the invention may be practiced otherwise than as specifically described herein.

The invention claimed is:

1. A method of producing a needle-shaped structure having a support substrate and a needle-shaped projection projected from the support substrate, the method comprising:

preparing a liquid material comprising a chitosan material and an acid;

applying the liquid material onto an intaglio plate having a needle-shaped recess;

solidifying the liquid material applied onto the intaglio plate such that a solidified article made from the liquid material is obtained;

separating the solidified article from the intaglio plate; and immersing separated solidified article in an aqueous alcohol solution which reduces the acid from the separated solidified article.

2. The method of producing a needle-shaped structure as defined in claim 1, wherein the aqueous alcohol solution comprises at least one alcohol selected from the group consisting of ethanol, methanol and propanol.

3. The method of producing a needle-shaped structure as defined in claim 2, wherein the aqueous alcohol solution has a concentration of 50-90 wt %.

4. The method of producing a needle-shaped structure as defined in claim 1, wherein the immersing comprises immersing the separated solidified article in a first aqueous alcohol solution of a higher concentration and then in a second aqueous alcohol solution of a lower concentration.

5. The method of producing a needle-shaped structure as defined in claim 1, wherein the chitosan material comprises at least one material selected from the group consisting of chitosan, chitin-chitosan, a chitin-chitosan derivative, glucosamine and a glucosamine derivative.

6. The method of producing a needle-shaped structure as defined in claim 1, wherein the acid comprises at least one selected from the group consisting of acetic acid, succinic acid, citric acid, lactic acid, tartaric acid, glyoxylic acid, pyruvic acid, oxalosuccinic acid, oxaloacetic acid, acetoacetic acid, levulinic acid, oxoglutaric acid, hydrochloric acid, sulfuric acid and a hydrate thereof.

7. A method of producing a needle-shaped structure having a support substrate and a needle-shaped projection projected from the support substrate, the method comprising:

preparing a liquid material comprising a chitosan material and an acid;

applying the liquid material onto an intaglio plate having a needle-shaped recess;

solidifying the liquid material applied onto the intaglio plate such that a solidified article made from the liquid material is obtained;

separating the solidified article from the intaglio plate; and placing separated solidified article in a solution acetylating the chitosan material in the separated solidified article.

8. The method of producing a needle-shaped structure as defined in claim 7, wherein the chitosan material comprises at least one material selected from the group consisting of chitosan, chitin-chitosan, a chitin-chitosan derivative, glucosamine and a glucosamine derivative.

9. The method of producing a needle-shaped structure as defined in claim 7, wherein the acid comprises at least one selected from the group consisting of acetic acid, succinic acid, citric acid, lactic acid, tartaric acid, glyoxylic acid, pyruvic acid, oxalosuccinic acid, oxaloacetic acid, acetoacetic acid, levulinic acid, oxoglutaric acid, hydrochloric acid, sulfuric acid and a hydrate thereof.

10. A method of producing a needle-shaped structure having a support substrate and a needle-shaped projection projected from the support substrate, the method comprising:
  preparing a liquid material comprising a chitosan material, a first acid, and a second acid;
  applying the liquid material onto an intaglio plate having a needle-shaped recess;
  solidifying the liquid material such that a solidified article made from the liquid material is obtained;
  separating the solidified article from the intaglio plate; and
  immersing separated solidified article in an aqueous alcohol solution,
  wherein the first acid is a tri- or higher valent carboxylic acid or a dicarboxylic acid having a number average molecular weight of not less than 110, and the second acid is a monocarboxylic acid or a dicarboxylic acid, having a number average molecular weight of less than 110.

11. The method of producing a needle-shaped structure as defined in claim 10, wherein the first acid is selected from the group consisting of citric acid, tartaric acid, fumaric acid and maleic acid, and the second acid is selected from the group consisting of formic acid, acetic acid, propionic acid, lactic acid, oxalic acid and malonic acid.

12. The method of producing a needle-shaped structure as defined in claim 10, wherein the first acid is citric acid.

13. The method of producing a needle-shaped structure as defined in claim 10, wherein the second acid is acetic acid.

14. The method of producing a needle-shaped structure as defined in claim 10, wherein a total amount of the first acid and the second acid is from 0.5 wt % to 40 wt % relative to the needle-shaped structure.

15. The method of producing a needle-shaped structure as defined in claim 10, wherein the aqueous alcohol solution comprises at least one alcohol selected from the group consisting of methanol, ethanol and propanol.

16. The method of producing a needle-shaped structure as defined in claim 10, wherein the aqueous alcohol solution has a concentration of 50 wt % to 90 wt %.

17. The method of producing a needle-shaped structure as defined in claim 10, wherein the chitosan material is at least one member selected from the group consisting of chitosan, chitin-chitosan, a chitin-chitosan derivative, glucosamine and a glucosamine derivative.

18. The method of producing a needle-shaped structure as defined in claim 10, wherein the projection and the support substrate are made of a material of a same composition.

19. The method of producing a needle-shaped structure as defined in claim 10, wherein the projection has a needle shape having a height of 10 μm to 1000 μm.

20. The method of producing a needle-shaped structure as defined in claim 7, wherein the solution includes acetic anhydride.

* * * * *